(12) United States Patent
Niese et al.

(10) Patent No.: US 8,435,253 B2
(45) Date of Patent: May 7, 2013

(54) MENISCAL REPAIR SYSTEMS AND METHODS

(75) Inventors: Brad A. Niese, Gilbert, AZ (US); Nicanor A. Domingo, Santa Clara, CA (US); Hoang P. Nguyen, Litchfield Park, AZ (US); Kevin N. Baird, Phoenix, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 0 days.

(21) Appl. No.: 13/274,132

(22) Filed: Oct. 14, 2011

(65) Prior Publication Data

US 2012/0035625 A1 Feb. 9, 2012

Related U.S. Application Data

(63) Continuation of application No. 12/603,232, filed on Oct. 21, 2009, now Pat. No. 8,177, 795.

(60) Provisional application No. 61/107,268, filed on Oct. 21, 2008.

(51) Int. Cl.
*A61B 17/04* (2006.01)
(52) U.S. Cl.
USPC .......................................................... 606/144
(58) Field of Classification Search .................. None
See application file for complete search history.

(56) References Cited

U.S. PATENT DOCUMENTS

| | | |
|---|---|---|
| 4,493,323 A | 1/1985 | Albright et al. |
| 5,133,723 A | 7/1992 | Li et al. |
| 5,178,628 A | 1/1993 | Otsuka et al. |
| 5,234,443 A | 8/1993 | Phan et al. |
| 5,250,055 A | 10/1993 | Moore et al. |
| 5,300,078 A | 4/1994 | Buelna |

(Continued)

FOREIGN PATENT DOCUMENTS

| | | |
|---|---|---|
| GB | 2325165 A | 11/1998 |
| WO | 9508950 A1 | 4/1995 |

(Continued)

OTHER PUBLICATIONS

Carter, Meniscus Repair 2007, Techniques in Knee Surgery, Dec. 2007, 233-241, 6-4.

(Continued)

*Primary Examiner* — Corrine M McDermott
*Assistant Examiner* — Son Dang
(74) *Attorney, Agent, or Firm* — Stout, Uxa, Buyan & Mullins, LLP; Donald E. Stout (57) ABSTRACT

A device for repairing a tear in a portion of tissue comprises a proximal actuator portion, a transfer needle extending distally from the proximal actuator portion and a catch needle extending distally from the proximal actuator portion. A suture needle is disposed in the transfer needle, and is extendable from the transfer needle toward the catch needle and retractable from the catch needle toward the transfer needle. An extendable catch plunger is disposed in the catch needle for capturing suture therein when it is transferred from the transfer needle. A retractable insertion sheath is provided for covering the transfer needle and the catch needle when the device is inserted into a procedural site. A depth limiting apparatus limits the depth of insertion of the needle into the procedural site.

4 Claims, 7 Drawing Sheets

U.S. PATENT DOCUMENTS

| | | | |
|---|---|---|---|
| 5,324,298 | A | 6/1994 | Phillips et al. |
| 5,330,488 | A | 7/1994 | Goldrath |
| 5,336,231 | A * | 8/1994 | Adair .............................. 606/148 |
| 5,364,407 | A | 11/1994 | Poll |
| 5,437,680 | A | 8/1995 | Yoon |
| 5,462,560 | A | 10/1995 | Stevens |
| 5,722,981 | A | 3/1998 | Stevens |
| 5,769,862 | A | 6/1998 | Kammerer et al. |
| 5,895,395 | A | 4/1999 | Yeung |
| 5,908,426 | A | 6/1999 | Pierce |
| 6,096,051 | A | 8/2000 | Kortenbach et al. |
| 6,162,209 | A | 12/2000 | Gobron et al. |
| 6,258,106 | B1 | 7/2001 | Leonard |
| 6,635,065 | B2 | 10/2003 | Burbank et al. |
| 6,638,286 | B1 * | 10/2003 | Burbank et al. .............. 606/157 |
| 6,884,249 | B2 | 4/2005 | May et al. |
| 6,997,933 | B2 | 2/2006 | Bittar |
| 7,048,749 | B2 | 5/2006 | Kortenbach et al. |
| 7,118,583 | B2 | 10/2006 | O'Quinn et al. |
| 7,232,448 | B2 | 6/2007 | Battles et al. |
| 7,306,613 | B2 | 12/2007 | Kawashima et al. |
| 7,326,222 | B2 | 2/2008 | Dreyfuss et al. |
| 7,381,210 | B2 | 6/2008 | Zarbatany et al. |
| 7,918,868 | B2 | 4/2011 | Marshall et al. |
| 2003/0181926 | A1 | 9/2003 | Dana et al. |
| 2004/0249393 | A1 | 12/2004 | Weisel et al. |
| 2005/0033325 | A1 | 2/2005 | May et al. |
| 2005/0187519 | A1 | 8/2005 | Harris et al. |
| 2005/0288690 | A1 | 12/2005 | Bourque et al. |
| 2006/0178680 | A1 | 8/2006 | Nelson et al. |
| 2006/0282088 | A1 | 12/2006 | Ryan |
| 2007/0149986 | A1 | 6/2007 | Morris et al. |
| 2007/0255306 | A1 | 11/2007 | Conlon et al. |
| 2008/0091219 | A1 | 4/2008 | Marshall et al. |
| 2008/0140091 | A1 | 6/2008 | DeDeyne et al. |
| 2008/0154286 | A1 | 6/2008 | Abbott et al. |
| 2009/0143806 | A1 | 6/2009 | Witt et al. |

FOREIGN PATENT DOCUMENTS

| | | |
|---|---|---|
| WO | 9747246 A1 | 12/1997 |
| WO | 9903402 A1 | 1/1999 |
| WO | 0126588 A2 | 4/2001 |
| WO | 03077771 A1 | 9/2003 |

OTHER PUBLICATIONS

Fukushima, et al., New Meniscus Repair by an All-Inside Knot Suture Technique, Arthroscopy: The Journal of Arthroscopic & Related Surgery, Jun. 2005, 768.e1-768.e10, 21-6.

In-Seop Park, New Meniscus Repair Technique for Peripheral Tears near the Posterior Tibial Attachment of the Posterior Horn of the Medial Meniscus, Arthroscopy: The Journal of Arthroscopic & Related Surgery, Aug. 2006, 908.e1-908.e4, 22-8.

Lambert, et al., Arthroscopic Meniscus Repair with Sutures: Outside-In, Sports Medicine & Arthroscopy Review. Mar. 2004, 25-36, 12-1.

Morgan, "All-Inside" Arthroscopic Meniscus Repair, Sports Medicine and Arthroscopy Review, Summer 1993, 1-3.

Prasad et al; Tribology of tungsten disulfide-nanocrystalline zinc oxide adaptive lubricant films from ambient to 500 oC; Wear, vol. 237, issue 2, Feb. 2000, pp. 186-196.

Reish, et al., FasT-Fix Meniscus Repair, Techniques in Knee Surgery, Sep. 2007, 161-167, 6-3.

Sgaglione, Meniscus Repair: Update on New Techniques, Techniques in Knee Surgery, Dec. 2002, 113-127,1-2.

* cited by examiner

MENISCAL REPAIR SYSTEMS AND METHODS

This application is a continuation application under 35 U.S.C. 120 of commonly assigned U.S. patent application Ser. No. 12/603,232, entitled Meniscal Repair Systems and Methods, filed Oct. 21, 2009, presently pending, which in turn claims the benefit under 35 U.S.C. 119(e) of the filing date of Provisional U.S. Application Ser. No. 61/107,268, entitled Suture Based All-Inside Meniscus Repair System, filed on Oct. 21, 2008. Each of the above referenced applications are expressly incorporated herein by reference, in its entirety.

The present application is also related to prior commonly assigned U.S. application Ser. No. 12/398,100, filed on Mar. 4, 2009, and entitled Arthroscopic Meniscal Repair Systems and Methods. This prior application is also herein expressly incorporated by reference, in its entirety.

BACKGROUND OF THE INVENTION

The present invention relates to surgical repair of meniscal tears, and more particularly to a unique arthroscopic handheld device and methods for repairing meniscal tears by passing suture within the meniscus through the tear.

There are two menisci in each knee, the medial meniscus, and the lateral meniscus, each of which comprises fibrocartilage. The menisci protect the articular cartilage on the surfaces of the femur and the tibia. Historically, torn portions of a meniscus were simply surgically removed. However, over time, it has become known in the field that removing substantial portions of the meniscus often accelerates the onset of osteoarthritis and other complications which develop when the shock absorbing meniscuses in the knee are absent. Most tears of the meniscus do not heal on their own, because of a very limited blood supply, but, using modern techniques, many tears can be surgically repaired, thus avoiding the need to remove meniscal portions.

Current meniscal repair methods and devices include both open surgical and arthroscopic techniques. Some repair approaches utilize suture only, others utilize anchors only, while still others are hybrid techniques which employ both suture and anchor devices.

Traditional prior art arthroscopic meniscal repair methods begin with a complicated suture only, "inside outside" technique. These techniques involve several access ports into the surgical site, and several instrument exchanges during the procedure, increasing surgical time and complexity. Because of this, the required surgical skill to effectively execute these arthroscopic procedures is quite high. A benefit to these conventional methods is that only suture is left behind at the procedural site, thus eliminating the risk of loose bodies in the knee space as well as abrasion to the articular cartilage from hard plastic or metal implants.

Another surgical technique that has developed involves a plastic implant with no suture. The implant has a dart shape to it with barbs that, when inserted into the meniscus, resist backing out. A benefit to this type of technology is that it avoids the need for numerous ports or instrument exchanges. This is a much easier method to execute than the suture-only method discussed above, but its downside is that it leaves a plastic head in the articular space, which causes abrasion to the femoral condyle articular cartilage.

Still another conventional meniscal repair technique that has been developed is a hybrid involving both an implant and suture. The benefit to this hybrid approach is that the practitioner gains the ease of the implant technique, as discussed above, but there is no exposed plastic implant in the articular space. The downside risk that still exists with this approach is that of a hard plastic loose body remaining at the procedural site. Should some sort of failure occur, the hard plastic implant may come loose and cause damage in the articular space.

What is needed, therefore, is an arthroscopic meniscal repair system and technique which combines the ease of the prior art implant procedures, while eliminating the risk that comes with a hard plastic implant.

SUMMARY OF THE INVENTION

The present invention comprises an all suture approach having the ease of a single working portal, a pre-tied knot, and a single handed device that includes a pre-tied knot. It duplicates the ease of the implant procedures discussed above, but eliminates the risk that comes with a hard plastic implant.

The inventive device passes suture from one needle to another, while both are positioned inside of the meniscus (intra-meniscal) as well as outside of the knee capsule. The suture has a pre-tied knot which is then utilized to draw the unstable portion of the torn meniscus back into contact with the stable portion, thereby stabilizing the meniscus and promoting healing.

More particularly, there is provided a device for repairing a tear in a portion of tissue, which comprises a proximal actuator portion, a transfer needle extending distally from the proximal actuator portion and having a distal tip for piercing tissue, and a catch needle extending distally from the proximal actuator portion and having a distal tip for piercing tissue. A suture needle is disposed in the transfer needle, and is extendable from the transfer needle toward the catch needle and retractable from the catch needle toward the transfer needle. An extendable catch plunger is disposed in the catch needle for capturing suture therein when it is transferred from the transfer needle. A retractable insertion sheath is provided for covering the transfer needle and the catch needle when the device is inserted into a procedural site. The proximal actuator portion comprises an insertion sheath actuator for retracting the insertion sheath, a suture needle advancement actuator for advancing and retracting the suture needle, and a catch plunger release mechanism for releasing the catch plunger for travel distally. The suture needle advancement actuator advantageously has an actuation position which also actuates the catch plunger release mechanism. In a preferred embodiment, this actuation position is when the actuator, which preferably comprises a lever, is fully depressed.

The transfer needle comprises a window disposed laterally thereon, through which the suture needle is extended or retracted. The catch needle, similarly, comprises a window disposed laterally thereon, through which the suture needle is extended or retracted. A second window is disposed on the catch needle on a side opposed to the side on which the first window is disposed, through which a distal end of the suture needle extends when the suture needle is fully extended into the catch needle.

The suture needle is sufficiently flexible that it attains a straightened configuration when housed within the transfer needle, and acquires a bend which assists in directing it toward the catch needle when the distal end of the suture needle extends out of the transfer needle.

An advantageous feature of the present invention is the inclusion of a depth limiting apparatus for limiting the depth of insertion of the needles into the procedural site. In one embodiment, the depth limiting apparatus comprises a depth gauge disposed on the proximal actuator portion, which preferably comprises a handle. In this embodiment, the insertion sheath actuator comprises a button which slides axially along a slot in the proximal actuator portion, and the depth gauge comprises graduated markings disposed along the slot, so that a practitioner can retract the sheath by sliding the insertion sheath actuator button a predetermined distance along the slot to control the depth of insertion of the device.

In an alternative embodiment, the depth limiting apparatus comprises a force feedback unit disposed on a distal end of the device. The force feedback unit preferably comprises a compression force element disposed on a distal end of one of the needles. The force feedback unit is preferably disposed on the shorter one of the needles, which is, in the current embodiments, the transfer needle. The compression force element comprises a plunger in the illustrated embodiment, though it may also comprise an electronic sensor, such as a strain gauge, or other suitable electronic or mechanical force sensing device. In this embodiment, the force feedback unit is coupled with a depth limiter which is movable distally along the device, responsive to a reduction of force on the force feedback unit. In some embodiments, it may be advantageous for each of the transfer needle and the catch needle to be curved, rather than straight, along their respective lengths.

In another aspect of the invention, there is provided a device for repairing a tear in a portion of tissue, which comprises a proximal actuator portion, a needle for dispensing suture into the tissue to be repaired, a retractable insertion sheath for covering the needle when the device is inserted into a procedural site, and a depth limiting apparatus for limiting the depth of insertion of the needle into the procedural site. The proximal actuator portion, which preferably comprises a handle, also comprises an insertion sheath actuator for retracting the insertion sheath.

In one embodiment, the depth limiting apparatus comprises a depth gauge disposed on the proximal actuator portion, which preferably comprises a handle. In this embodiment, the insertion sheath actuator comprises a button which slides axially along a slot in the proximal actuator portion, and the depth gauge comprises graduated markings disposed along the slot, so that a practitioner can retract the sheath by sliding the insertion sheath actuator button a predetermined distance along the slot to control the depth of insertion of the device.

In an alternative embodiment, the depth limiting apparatus comprises a force feedback unit disposed on a distal end of the device. The force feedback unit preferably comprises a compression force element disposed on a distal end of the needle. The compression force element comprises a plunger in the illustrated embodiment, though it may also comprise an electronic sensor, such as a strain gauge, or other suitable electronic or mechanical force sensing device. In this embodiment, the force feedback unit is coupled with a depth limiter which is movable distally along the device, responsive to a reduction of force on the force feedback unit.

In still another aspect of the invention, there is disclosed a method for repairing a tear in a portion of tissue, which comprises a step of inserting a device comprising a proximal actuator portion and a distal needle portion into a procedural site. A sheath covering the needle is retracted proximally to expose the distal end of the needle, followed by a step of advancing the needle into the tissue to be repaired, so that a distal end of the needle is disposed beyond the tear, until a depth limiting structure prevents further advancement of the needle. Further steps include creating a suture loop in the tissue to repair the tear, withdrawing the needle proximally from the procedural site, and using a pre-tied knot to cinch the suture loop and thereby repair the tear.

The advancing step of the disclosed method comprises advancing a pair of needles into the tissue to be repaired, and the suture loop creating step is performed by dispensing suture from one of the needles into a second of the needles, and then releasing a catch plunger to move distally and clamp the suture to retain it in the second needle.

The depth limiting structure comprises a distal end of the sheath, and, in one disclosed method, the sheath retracting step includes a step of determining a distance through which the sheath is retracted by consulting a depth gauge disposed on the proximal actuator portion. In an alternative disclosed method, the depth limiting structure comprises a depth limiter which is movable distally along the device toward the tissue to be repaired responsive to a release of force on a force feedback unit disposed on a distal end of the needle.

The invention, together with additional features and advantages thereof, may best be understood by reference to the following description taken in conjunction with the accompanying illustrative drawing.

DESCRIPTION OF THE PREFERRED EMBODIMENT

Figure 1:
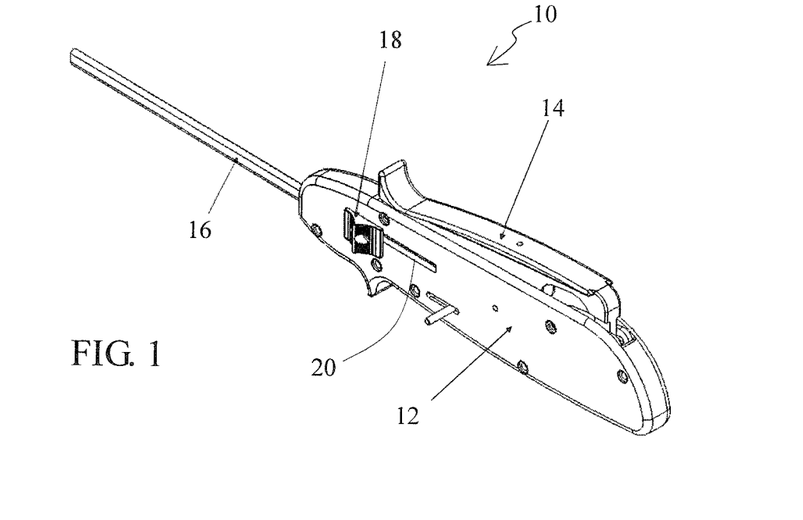
FIG. 1 is an isometric view showing one embodiment of a meniscal repair device constructed in accordance with the principles of the present invention.

Referring now more particularly to the drawings, there is shown in FIG. 1 an embodiment of a meniscal repair device 10 constructed in accordance with the principles of the present invention. The device 10 comprises a handle 12 which has a suture needle advancement lever 14. Distally of the handle 12 is provided a depth limiter/insertion sheath 16. A depth limiter/insertion sheath actuation button 18 is disposed on the handle 12.

Figure 2:
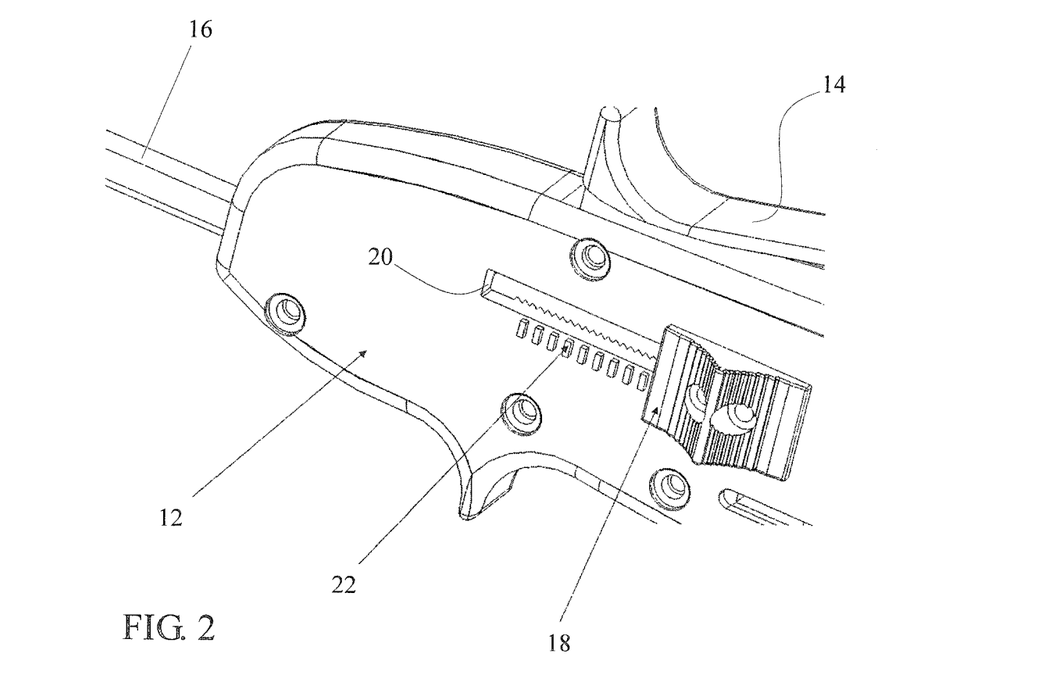
FIG. 2 is an isometric enlarged view of portions of the handle of the meniscal repair device of FIG. 1.
Figure 7:
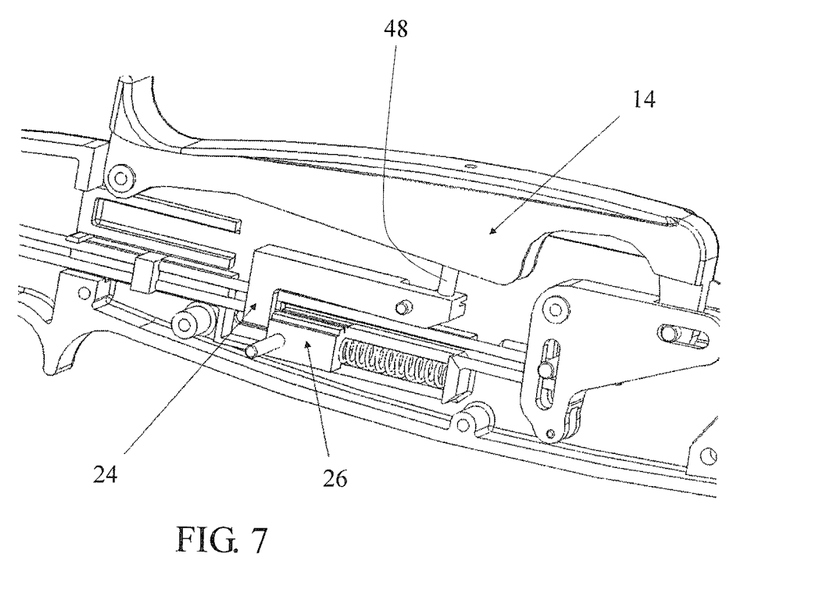
FIG. 7 is an enlarged isometric view of the handle of the meniscal repair device of the present invention, with the cover removed to show the interior construction thereof.

Now with reference to FIGS. 2 and 7, in addition to FIG. 1, additional constructional details of the handle 12 are illustrated. As shown particularly in FIG. 2, the depth limiter/insertion sheath actuation button 18 travels axially within a slot 20. A depth gauge 22 is provided for purposes which will be described below. In FIG. 7, wherein the cover of the handle has been removed to reveal the internal construction of the handle 12, it can be seen that a piston retention lever 24 and a catch spring piston 26 are disposed therein.

Figure 6:
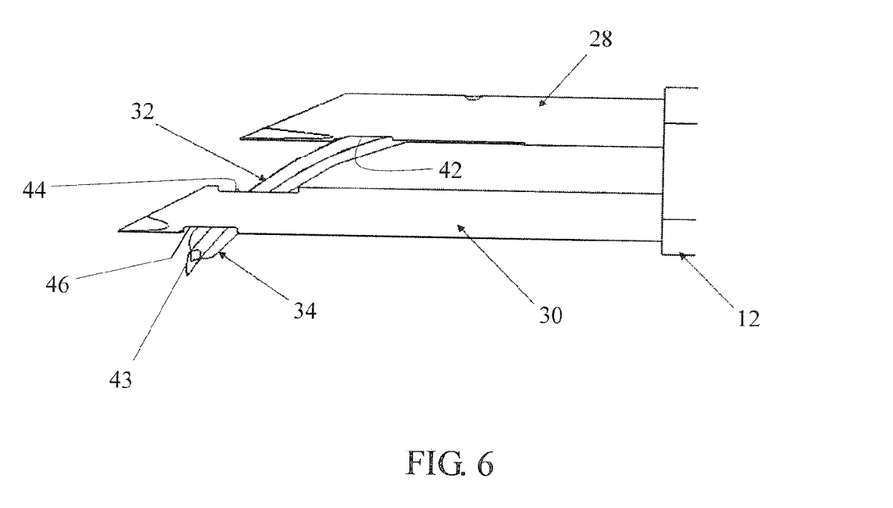
FIG. 6 is a detail plan view showing the portion of FIG. 5 which is denoted by the letter A.
Figure 8:
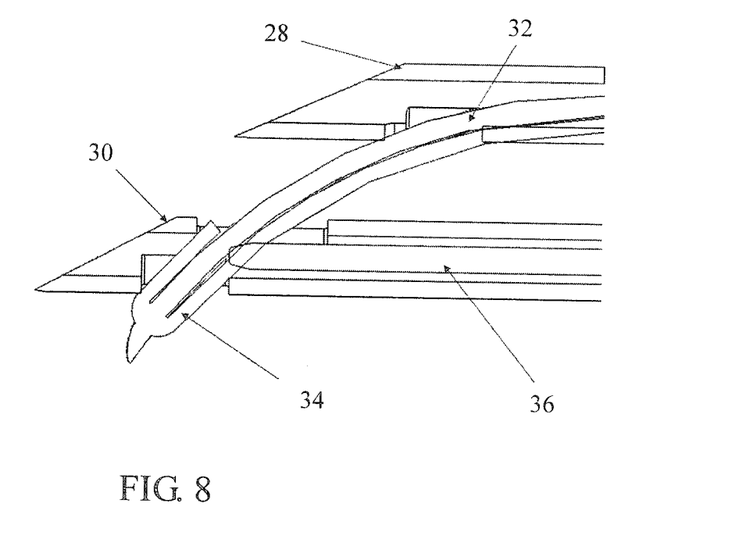
FIG. 8 is an enlarged plan view of the distal end of the meniscal repair device of the invention, illustrating the suture needle as it is driven from the transfer needle to the catch needle.

In FIGS. 6 and 8, the distal end of the meniscal repair device 10 is illustrated. The distal end of the device 10 comprises a transfer needle 28 and a catch needle 30. A suture needle 32 is extendable from the transfer needle 28, as shown in FIG. 6, for carrying suture 34 toward the catch needle 30 for purposes to be described below. A catch plunger 36 is also provided, as shown in FIG. 8.

Figure 3:
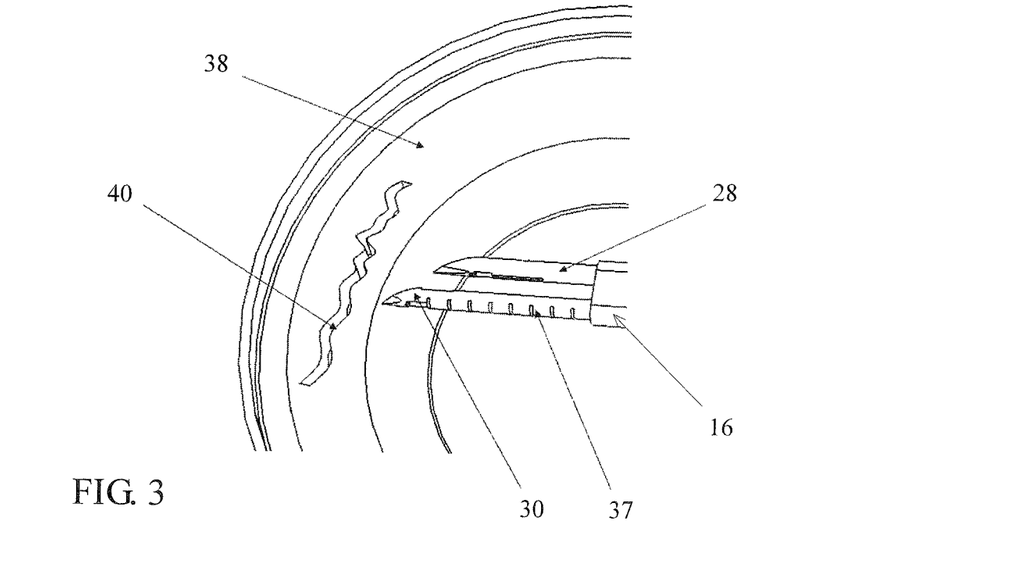
FIG. 3 is a plan view illustrating a distal end of the meniscal repair device illustrated in FIGS. 1 and 2 as it approaches a torn meniscus to be repaired.

Now, with reference to the drawing figures, a representative procedure which may be performed using the inventive device 10 will be described. As noted above, in FIG. 1 the device 10 is illustrated as it is configured prior to insertion into a patient. Once the practitioner has measured the depth from the needle insertion point to the approximate needle exit point, the device can be inserted into the patient's knee. The sheath 16 is retractable, and covers the transfer needle 28 and catch needle 30 while the device is introduced into the patient, for the purpose of protecting the patient from being injured by the needle points. The device 10 can be inserted into the patient's knee by any suitable means, such as a cannula or other type of introducer channel. Once the device 10 is inserted to the procedural site, the practitioner then retracts the sheath 16 by pulling the sheath actuation button 18 backwards, and lets the sheath stop at the desired depth of penetration, which is indicated by the sliding depth gauge 22 on the handle 12. Another depth gauge 37, with graduated markings corresponding to those on the depth gauge 22, is disposed on the distal end of the catch needle 30, as shown in FIG. 3. This depth gauge is visible arthroscopically during the course of the procedure.

Figure 4:
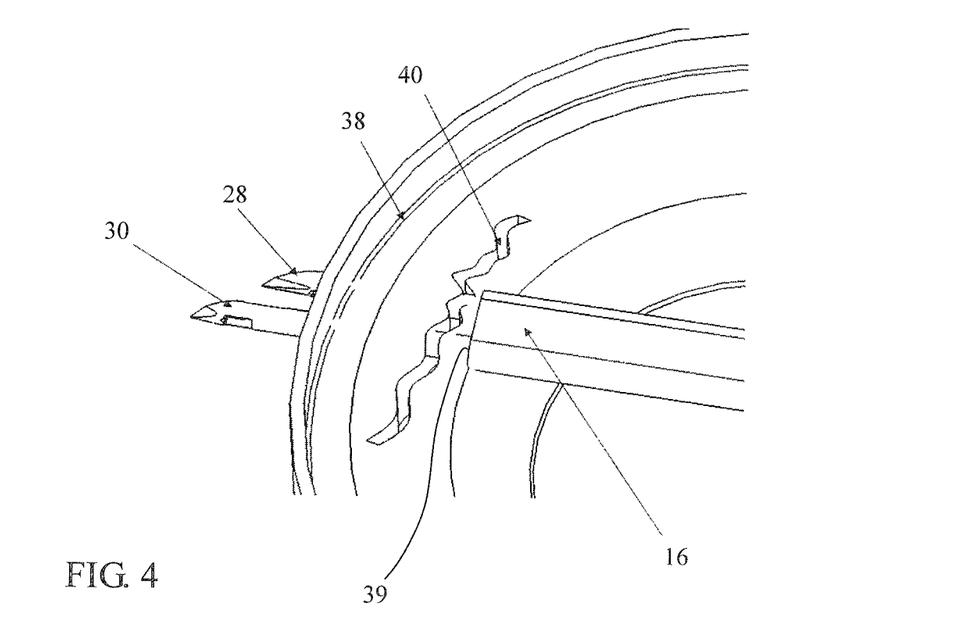
FIG. 4 is a plan view similar to FIG. 3, illustrating the distal end of the meniscal repair device after it has advanced into and through the meniscus.
Figure 5:
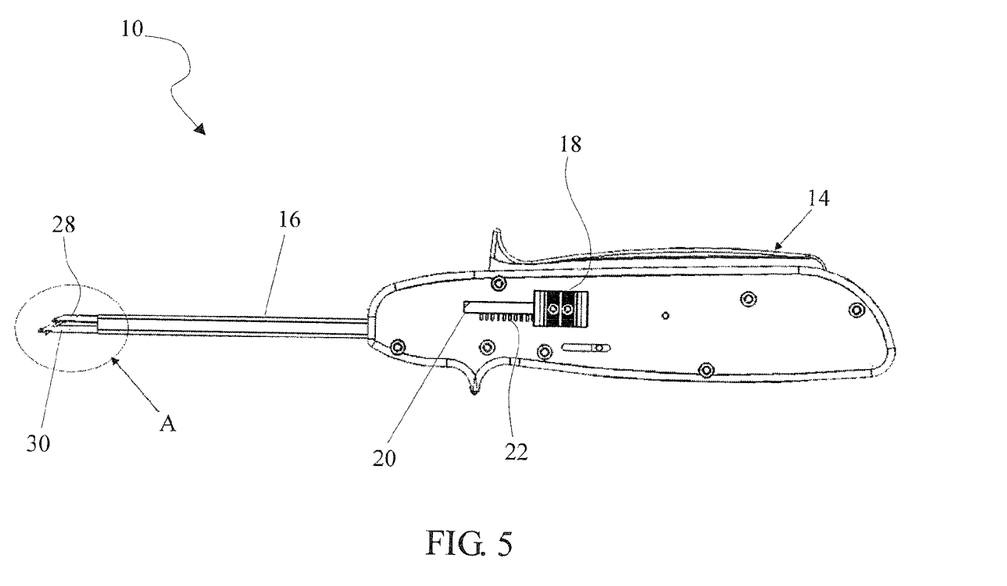
FIG. 5 is a plan view of the meniscal repair device of the present invention, showing the device as it is about to be actuated after the distal end has been positioned at the procedural site as shown in FIG. 4.

The practitioner continues to insert the device 10 until the sheath 16 comes into contact with the meniscus 38, at which point the device will be unable to go any deeper. This step of insertion is illustrated in sequential FIGS. 3 and 5. Note that in FIG. 4, distal progress of the device 10 has stopped, because the distal end 39 of the sheath 16 is in contact with the meniscus 38.

Once the needles 28 and 30 have been fully inserted through the meniscal tear 40 to be repaired, the practitioner then squeezes the suture needle advancement lever 14 downwardly toward the body of the handle 12. This action drives the suture needle 32 from the transfer needle 28 and into the catch needle 30, as shown in FIG. 6. The suture needle 32 exits the transfer needle 28 through a transfer needle window 42 and a distal end 43 of the suture needle 32 enters the catch needle 30 through a first suture catch window 44. As the suture needle 32 continues its travel, the distal end 43 thereof exits the catch needle 30 through a second suture catch window 46. In order to function in the described manner, the suture needle preferably has a needle point or piercing tip, as shown, configured to give it the ability to pierce through the meniscus 38, and is sufficiently flexible so that it can be housed in a straightened configuration inside the transfer needle 28 prior to actuation and then take the necessary bend during deployment. The suture needle 32 can be made of a spring tempered stainless steel or a shape memory type of alloy such as nitinol. It can be manufactured with processes that pre-shape it, thereby allowing it to be advanced out of the transfer needle 28 and into the catch needle 30.

Once the suture needle advancement lever 14 has been squeezed fully, the catch plunger 36 inside the catch needle 30 is actuated by releasing the catch spring piston 26 in the handle 12. A protrusion 48 on the suture needle advancement lever 14 hits the piston retention lever 24, which releases the catch spring piston 26 (FIG. 7). The catch spring piston 26 drives the catch plunger 36 toward the suture 34 and the suture needle 32. The catch plunger 36 advances distally sufficiently to collide with the suture 34 and pin the suture against the suture needle 32.

Figure 9:
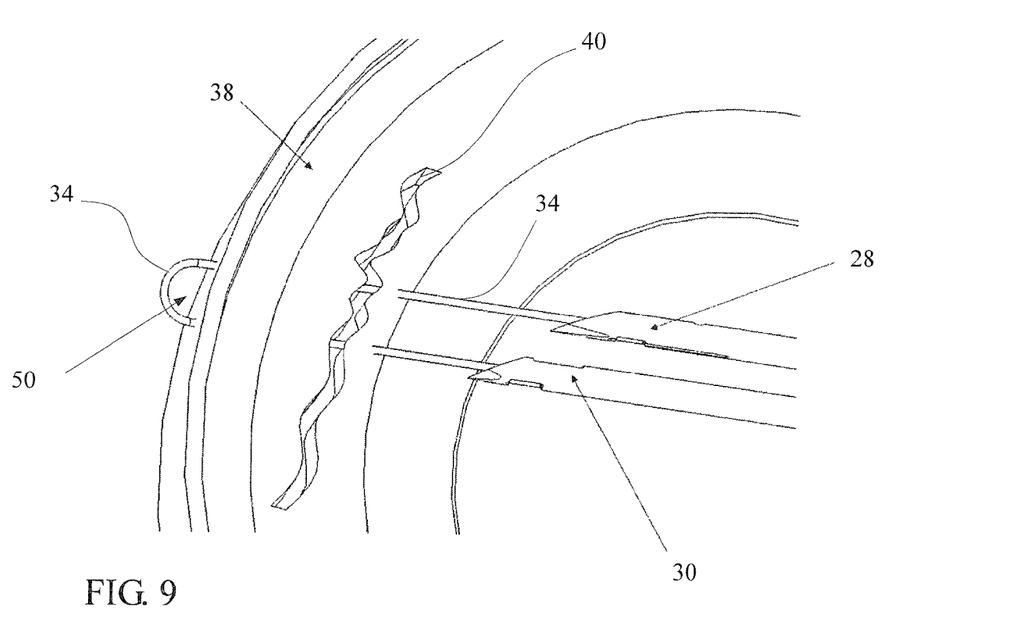
FIG. 9 is an isometric view illustrating the procedural site as the inventive device is withdrawn therefrom to loop the suture through the meniscus.

Releasing the suture needle advancement lever 14 retracts the suture needle 32, leaving the suture 34 behind inside of the catch needle 30. Once this step is completed, the device 10 is retracted from the patient. Since the suture 34 entered the patient attached to the transfer needle 28, and has now been passed to the catch needle 30, a suture loop 50, as shown in FIG. 9, has now been created through the meniscus 38.

Figure 10:
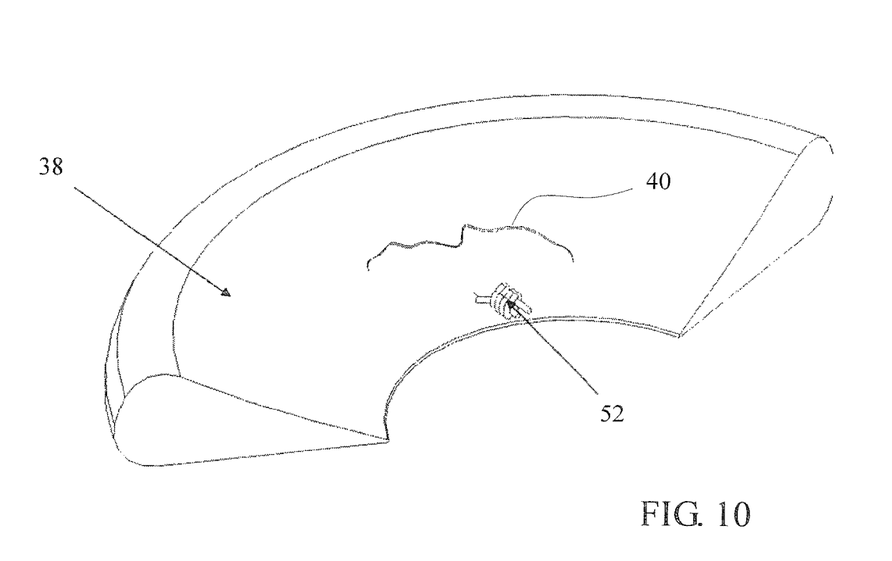
FIG. 10 is an isometric view showing the repaired meniscus after a pre-tied knot has been secured in place to stabilize the tear.

At this juncture, a pre-tied knot 52 is pulled tightly against the meniscus 38 and provides fixation for healing of the now closed meniscal tear 40. This pre-tied knot may be initially disposed on the instrument 10, and then slid down the suture legs 34 distally until it contacts the meniscus. The long ends of the suture 34, which extend proximally from the procedural site, are then cut off once the knot 52 is in place. The repaired meniscus 38 is shown in FIG. 10.

Figure 11:
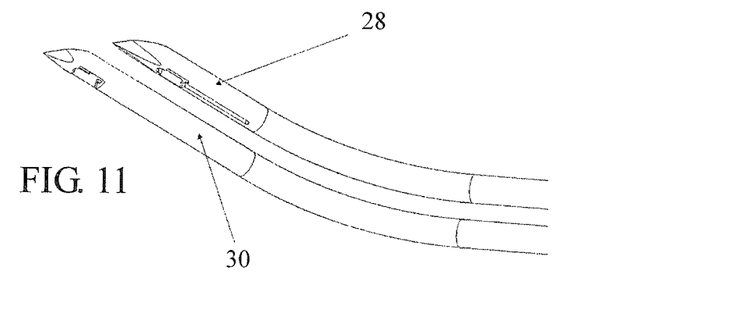
FIGS. 11-13 are views illustrating three different potential curve options for enhancing maneuverability of the inventive device.
Figure 12:
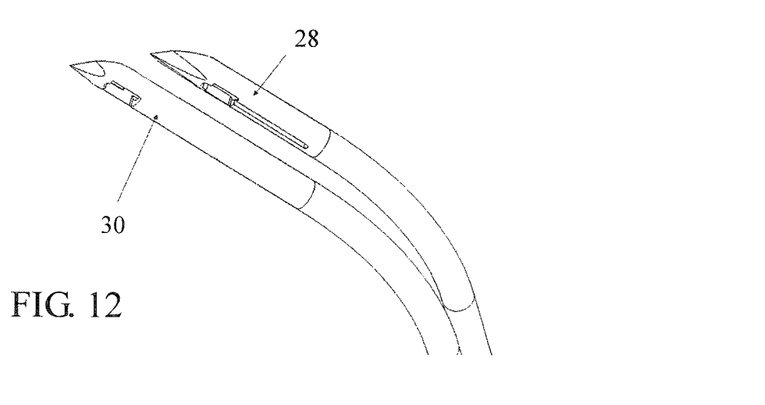
Figure 13:
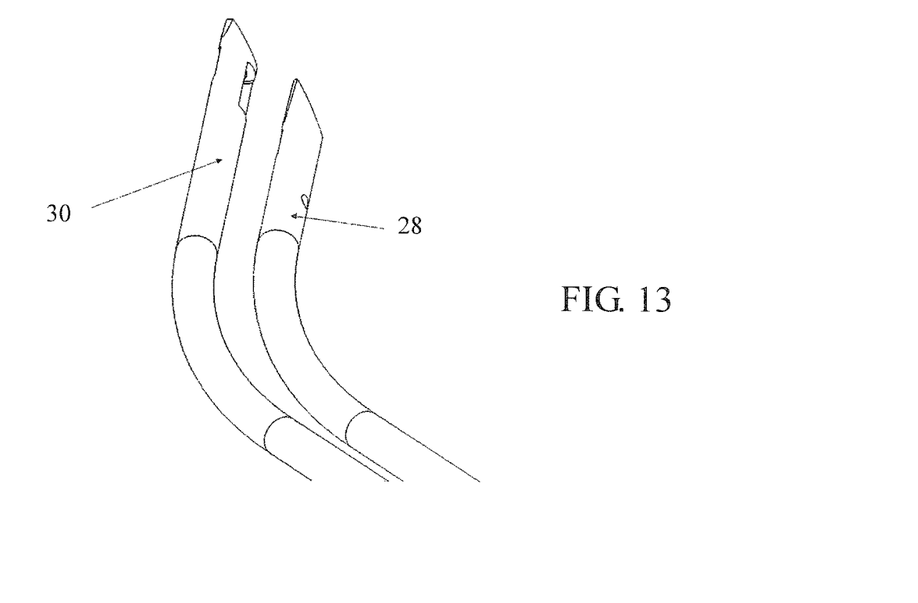

FIGS. 11-13 illustrate three alternative needle embodiments, wherein the transfer needle 28 and the catch needle 30 are curved, rather than straight, as in the embodiment illustrated in FIGS. 1-10. Curves of the type disclosed in FIGS. 11-13 may be used to facilitate maneuvering beneath the femoral condyles.

Currently, the curves being explored are fixed during the manufacturing process. The cavity between the femoral condyle and the meniscus can be quite tight, and as such, in some embodiments of the invention, it can be advantageous for the curves to be adjusted by the practitioner, as needed, to maneuver inside of the joint space.

The approach shown in the figures thus far involve a horizontal stitch placement. However, it is possible, and has been achieved by the inventor in cadaver tissue, to rotate the needle into a vertical position and to place the stitch. There are instances where this would be an advantageous approach from a repair strength standpoint.

The bevel orientation of the needles is currently fixed. However, the bevels can be changed in order to make the device easier to use.

The shield/depth limiter shown and described above is one approach with regards to limiting the insertion depth of the device into the meniscus.

Within the scope of the present invention, it is possible to add a tag or barb onto the end of the suture 34, which will provide a good piercing point, as an alternative to the current suture needle approach. A hard feature may also be employed, which makes capture of the suture easier and more resistant to letting go prematurely.

The device is not presently re-loadable in the operating room. However, in alternative embodiments, the device may be designed to be easily re-loadable.

The width of the stitch is an important factor in determining the strength of the final repair. Basically, the wider the stitch, the stronger the repair will be. The width of the stitch, in some invention embodiments, is adjustable in the operating room. This way the practitioner is able to determine the best stitch width for the given situation.

The bevel orientation of the needles is currently fixed. However, these may change in order to make the device easier to use.

The sheath/depth limiter described and shown is one alternative with regard to limiting the insertion depth of the device into the meniscus. In the present invention, there is a stationary steel component which joins the needles together and holds their orientation. This component can be made to slide along the axis of the needle. By doing this, it can be utilized for depth limitation.

Other adjustable depth limiting devices may include inflatable structures, absorbing cushions, ball detents, and metal crush sleeves, for examples.

A different depth limiting approach is to move the needles in and out of a stationary sheath which provides depth limiting. This way, the needles may be completely shrouded upon entering the patient without need for additional insertion sheaths.

Figure 14:
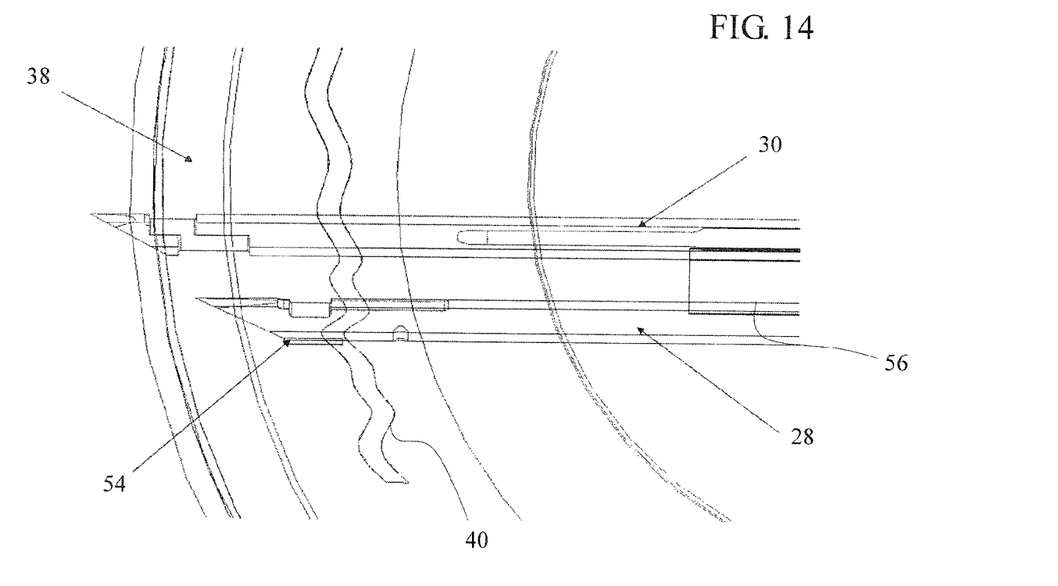
FIG. 14 is a plan view illustrating an alternative force feedback depth limitation feature for the present invention, wherein the plunger element is under compression.
Figure 15:
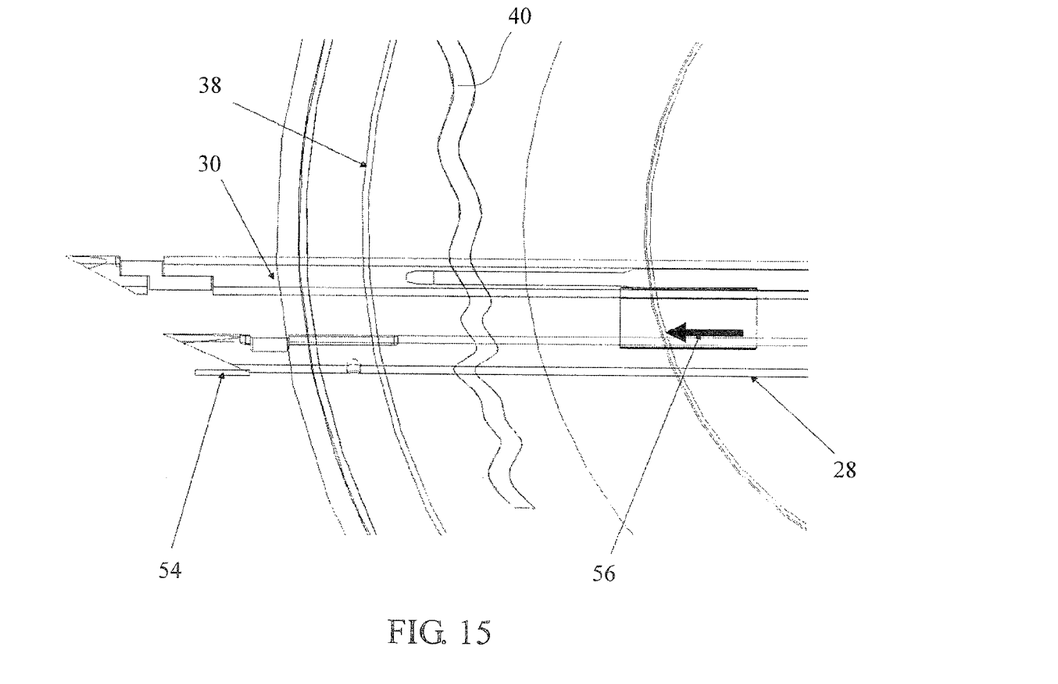
FIG. 15 is a plan view similar to FIG. 14, illustrating release of the plunger element upon exiting of the device from the distal end of the meniscus.

Still another approach is to utilize a method of force feedback to determine whether the needle tips have gotten past the outer surface of the meniscus and into the capsule. FIGS. 14 and 15 illustrate such a method sequentially. A compression force (plunger) element 54 may be placed on the distal end of the shorter transfer needle 28. When the plunger 54 exits the meniscus and enters the capsule, the force on the needle reduces, and the plunger then springs forward and releases a mechanism which drives a depth limiter 56 distally against the meniscus (FIG. 15) and thus prevents further distal penetration of the needles.

Of course, while the foregoing invention has been disclosed in connection with the repair of meniscal tissue, it will be recognized that the inventive principles are applicable to many other instances wherein it is desired to repair a tear in a portion of soft tissue.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A method for repairing a tear in a portion of tissue, said method comprising:
    inserting a device comprising a proximal actuator portion and a needle having a distal needle portion into a procedural site;
    retracting a sheath covering said needle proximally to expose the distal needle portion;
    advancing the needle into the tissue to be repaired, so that a distal end of the distal needle portion is disposed beyond the tear, until a depth limiting structure prevents further advancement of the needle, wherein the advancing step comprises advancing a pair of needles into the tissue to be repaired, and the suture loop creating step is performed by dispensing suture from a first one of the needles into a second of the needles, and then releasing a catch plunger to move distally and clamp the suture to retain it in the second needle, wherein the catch plunger is disposed in the second needle and is extendable within the second needle to clamp the suture within the second needle;
    creating a suture loop in said tissue to repair the tear;
    withdrawing the needle proximally from the procedural site; and
    using a pre-tied knot to cinch the suture loop and thereby repair the tear.

2. The method as recited in claim 1, wherein the depth limiting structure comprises a distal end of the sheath, and the sheath retracting step includes a step of determining a distance through which the sheath is retracted by consulting a depth gauge disposed on the proximal actuator portion.

3. The method as recited in claim 1, wherein the depth limiting structure comprises a depth limiter which is movable distally along the device toward the tissue to be repaired responsive to a release of force on a force feedback unit disposed on a distal end of the needle.

4. The method as recited in claim 1, wherein the suture is dispensed, during the suture loop creating step, using a suture needle which is disposed in the first needle and is extendable from the first needle toward the second needle and retractable from the second needle toward the first needle.

* * * * *